United States Patent [19]

Minneman

[11] Patent Number: 5,533,524
[45] Date of Patent: Jul. 9, 1996

[54] MOUTHGUARD HAVING AN EXTRA-ORAL PORTION AND AN INTRA-ORAL PORTION

[76] Inventor: Sue A. F. Minneman, 6250-202 St. Regis Cir., Raleigh, N.C. 27606

[21] Appl. No.: 527,105

[22] Filed: Sep. 12, 1995

Related U.S. Application Data

[62] Division of Ser. No. 253,099, Jun. 2, 1994, Pat. No. 5,469,865.

[51] Int. Cl.⁶ ..................................................... A61C 5/14
[52] U.S. Cl. .......................... 128/859; 128/861; 128/862
[58] Field of Search .......................... 128/848, 859–862; 2/2

[56] References Cited

U.S. PATENT DOCUMENTS

| 165,584 | 7/1875 | Hopfen . | |
|---|---|---|---|
| 291,071 | 1/1884 | Mitchell . | |
| 779,360 | 1/1905 | Grummann . | |
| 803,474 | 10/1905 | Dennis . | |
| 1,270,565 | 6/1918 | Teter . | |
| 1,302,004 | 4/1919 | Brown . | |
| 1,371,029 | 3/1921 | Jennings . | |
| 1,466,559 | 8/1923 | Purdy . | |
| 1,498,810 | 6/1924 | Poe . | |
| 1,586,499 | 5/1926 | Worth . | |
| 1,818,146 | 8/1931 | Maker . | |
| 1,934,688 | 11/1933 | Ackerman | 32/5 |
| 2,360,193 | 10/1944 | Boothby et al. | 128/147 |
| 2,459,273 | 1/1949 | Freedland | 128/12 |
| 2,521,084 | 9/1950 | Oberto | 128/141 |
| 2,590,118 | 3/1952 | Oddo, Jr. | 128/136 |
| 2,614,560 | 10/1952 | Lee | 128/136 |
| 2,669,988 | 2/1954 | Carpenter | 128/136 |
| 2,678,043 | 5/1954 | Stark | 128/136 |
| 2,685,133 | 8/1954 | Greene et al. | 32/2 |
| 2,693,182 | 11/1954 | Phillips | 128/208 |
| 2,694,397 | 11/1954 | Herms | 128/861 |
| 2,705,492 | 4/1955 | Chandler | 128/136 |
| 2,706,478 | 4/1955 | Porter | 128/136 |
| 2,750,941 | 6/1956 | Cathcart | 128/136 |
| 2,833,278 | 5/1958 | Ross | 128/136 |
| 2,857,908 | 10/1958 | Cornfield | 128/15 |
| 2,882,893 | 4/1959 | Godfroy | 128/136 |
| 3,014,286 | 12/1961 | Hricak | 35/35 |
| 3,016,052 | 1/1962 | Zubren | 128/136 |
| 3,060,935 | 10/1962 | Riddell | 128/260 |
| 3,073,300 | 1/1963 | Berghash | 128/136 |
| 3,103,217 | 9/1963 | Butler et al. | 128/136 |
| 3,124,129 | 3/1964 | Grossberg | 128/136 |
| 3,126,002 | 6/1965 | Owens | 128/136 |
| 3,187,746 | 6/1965 | Gerber | 128/136 |
| 3,223,085 | 12/1965 | Gores et al. | 128/136 |
| 3,236,235 | 2/1966 | Jacobs | 128/136 |
| 3,247,844 | 4/1966 | Berghash | 128/136 |
| 3,286,576 | 11/1966 | West | 84/466 |
| 3,293,748 | 12/1966 | Skinner | 32/19 |
| 3,307,539 | 3/1967 | Peterson | 128/136 |
| 3,319,626 | 5/1967 | Lindsay | 128/136 |
| 3,339,547 | 9/1967 | Drabkowski | 128/260 |
| 3,385,291 | 5/1968 | Martin | 128/62 |
| 3,416,527 | 12/1968 | Hoef | 128/260 |
| 3,496,936 | 2/1970 | Gores | 128/136 |
| 3,513,838 | 5/1970 | Foderick et al. | 128/136 |
| 3,682,164 | 8/1972 | Miller | 128/136 |
| 3,971,370 | 7/1976 | Halford et al. | 128/136 |
| 4,041,937 | 8/1977 | Diaz | 128/15 |
| 4,112,936 | 9/1978 | Blachly | 128/136 |
| 4,867,147 | 9/1989 | Davis | 128/861 |

(List continued on next page.)

FOREIGN PATENT DOCUMENTS

698570 10/1953 United Kingdom ................... 81/20 B

Primary Examiner—Michael A. Brown
Attorney, Agent, or Firm—Olive & Olive

[57] ABSTRACT

A mouthguard which has a generally U-shaped intra-oral portion for placement in a patient's mouth and a generally U-shaped extra-oral portion which is placed outside the patient's mouth. The intra-oral portion may be shaped for bilateral placement between the upper and lower anterior teeth or the upper and lower posterior teeth, or for unilateral placement between the upper and lower canine teeth. There are narrow indentations between the arms of the extra-oral and intra-oral portions.

5 Claims, 6 Drawing Sheets

U.S. PATENT DOCUMENTS

| | | | |
|---|---|---|---|
| 4,994,947 | 7/1990 | Newman | 424/435 |
| 5,031,638 | 7/1991 | Castaldi | 128/861 |
| 5,052,410 | 10/1991 | Stubbes | 128/859 |
| 5,063,940 | 11/1991 | Adell | 128/861 |
| 5,082,007 | 1/1992 | Adell | 128/861 |
| 5,235,991 | 8/1993 | Minneman | 128/861 |
| 5,320,114 | 6/1994 | Kittelsen | 128/861 |
| 5,381,783 | 1/1995 | Hintz | 128/861 |

MOUTHGUARD HAVING AN EXTRA-ORAL PORTION AND AN INTRA-ORAL PORTION

This application is a division of Ser. No. 08/253,099 filed Jun. 2, 1994, now U.S. Pat. No. 5,469,865.

BACKGROUND OF THE INVENTION

1. Field of the Invention

This invention relates to oral devices, appliances, mouthguards and mouth props used to prevent oral injuries of the soft tissues, i.e., lips, cheeks, tongue, and of the teeth in comatose, decerebrate and generally anesthetized patients as well as dentally anesthetized patients.

2. Description of the Related Art

Uncontrolled, uncoordinated biting, chewing, grinding and clenching movements of the mandible may cause damage to oral soft tissues, such as the tongue, cheek, mucosa, and lips, if these tissues become entrapped or impinged between the upper and lower teeth. Uncontrolled, uncoordinated biting, chewing, grinding and clenching movements of the jaws can also cause teeth and dental restorations to fracture and break. These consequences of oral injuries can precipitate the introduction of blood, debris and other material in the oral cavity and present a risk to the respiratory system of the injured patient.

Persons who are comatose, heavily anesthetized, or decerebrate can unconsciously display powerful oral movements which are extremely difficult to control and often cause traumatic lacerations and mutilation of the tongue, lips and cheeks. Persons whose mandibular nerve, lingual nerve and/or mental nerve is locally anesthetized for dental procedures, i.e., dental restorations and extractions, have a period of altered sensations to pain and pressure in their tongues, cheeks, and lower lips. Children and the developmentally disabled frequently chew and bite these anesthetized oral soft tissues causing lacerations and mutilation of tissues which may lead to permanent disfigurement.

Several oral devices have been tried in attempts to prevent further oral trauma in patients who have bitten themselves. The devices for the patients whose conditions are considered long-term, i.e. the comatose and decerebrate are of a more permanent nature. One device uses intermaxillary fixation with arch wires in conjunction with hard oral acrylic devices. Some of the problems which can occur when the maxilla and mandible are wired together in this fashion include the inability of the patient to breath through his oral cavity, the inability of the patient's caregiver to maintain a patient airway by suctioning mucus and oral secretions from the patient's pharynx and the inability of the caregiver to deliver adequate oral hygiene measures to the patient. Tongue blades padded with gauze and wrapped with tape, hard and soft rubber and plastic mouth props, and flexible and inflexible metal and plastic airways have been used. Some problems which occur with these devices include an inability to keep them in their intended positions, between the patient's upper and lower teeth, unless a caregiver is managing the placement and positioning of the device at all times. If the patient opens wider than the device, as when yawning, the device may move into his throat or airway. If the patient thrusts his tongue forward against the device, he can push it out of his mouth. If the patient grinds his mandible from side to side he can also work the device out of his mouth or into his throat or airway. Customized soft and hard acrylic biteguards which cover the occlusal, facial and lingual surfaces of the upper and lower teeth have been used. In order to customize the acrylic biteguards to fit the patient's teeth and oral structures, impressions or imprints of the patient's dental arches must be obtained. The dental impression procedure can present risks to the patient's airway should the soft puttylike material be aspirated by the patient. The customized soft and hard acrylic biteguards can be dislodged from the teeth with tongue movements and grinding movements and create foreign body risks to the patient's airway and throat.

The protection used in the patients whose sensations to pain and pressure have been temporarily altered as a result of local mandibular dental anesthesia is frequently in the form of gauze padding or cotton rolls placed between the teeth on the non-anesthetized side of the mouth. By propping the teeth opened, oral tissues are not easily bitten. This protective procedure does not work well with patients who are unable to understand the logic of the instructions nor with those who are unable to comply with the instructions, i.e. children and the mentally handicapped. Therefore, the gauze padding and cotton rolls are frequently displaced, expelled and occasionally aspirated or swallowed.

Many different mouthguards have been designed to prevent mouth injury to patients. Some of these guards also have features particularly useful in keeping the throat of a patient under general anesthesia from becoming obstructed. Many of the prior mouthguards have complicated structures to accomplish these purposes.

The early patent of Freedland (U.S. Pat. No. 2,459,273) is for a shock therapy mouthguard with a rubbery pad mounted between the ends of a rigid handle. A longitudinal passage is formed on top of the handle on the pad. The lower teeth of a patient are placed between two arcuate projections on the lower surface of the pad. The disclosure of this patent and all other patents and publications cited herein is hereby incorporated herein by reference.

Other devices are simpler in form, being essentially a single U-shape (U.S. Pat. No. 4,867,147 of Davis) or Y-shape (U.S. Pat. No. 2,694,397 of Herms for a mouth prop with a flat handle having a recessed area between the handle and the arms positioned so that the upper front teeth do not touch the handle when the molars are positioned on the arms of the prop and having optional pads added to the top surface of the arms).

Even simpler is the disposable BITE™ jawlock of U.S. Pat. No. 3,971,370 which is simply a tongue depressing stick with a polyethylene pad at one end. For use in soft tissue oral protection and jaw positioning, a BITE™ jawlock is placed on one or both sides of the oral cavity. Because the BITE™ jawlock does not fill the oral cavity, it is often difficult to keep the two jawlocks in the correct place to prevent patient injury.

The patent of Ross (U.S. Pat. No. 2,833,278) is for a mouthguard comprising an upright "H" form in multiple planes. The teeth of the patient rest on the one portion and do not rest on the portions that extend above and below the top and bottom of the portion on which the teeth rest.

Many teeth protectors have a horizontal surface for the teeth to bite upon and a vertical surface extending upward from the front of the horizontal surface. See, for example, Brown (U.S. Pat. No. 1,302,004).

Some of the tooth guards have elaborate molded flanges for protection of the front teeth and an attached breathing tube (See U.S. Pat. Nos. 2,669,988 of Carpenter; 2,521,084 of Oberto; 2,882,893 of Godfroy; and 4,112,936 of Blachly).

Another standard type of teeth protector has a channel which surrounds the teeth, and in some cases also assists in treating the teeth. See, for example, Newman (U.S. Pat. No. 4,944,947: a device with recessed areas between surrounding side areas in which to place the teeth; Grossberg (U.S. Pat. No. 3,124,129); Martin (U.S. Pat. No. 3,385,291: the device has an upper and lower channel which partially surrounds the teeth with a rubber like material in the channels molded to conform with the gums and sides of the teeth); Hoef (U.S. Pat. No. 3,416,527: a U-shaped channel fabricated from a substance which will retain a liquid, with a liquid impermeable backing); Riddell (U.S. Pat. No. 3,060,935); and Castaldi (U.S. Pat. No. 5,031,638).

Other mouthguards are particularly designed for use by athletes, and are primarily made to surround and protect all of the player's teeth, for example, U.S. Pat. Nos. 3,496,939 of Gores and 5,082,007 of Adell. Other mouthguards are designed for use by persons undergoing operations requiring intubation, for example, U.S. Pat. No. 3,513,838 of Foderick, or to firmly depress and hold a patient's tongue, for example, U.S. Pat. No. 4,041,937 of Diaz.

Some of the devices are also designed to keep the tongue, lips and cheeks away from the teeth. See for example, Lee (U.S. Pat. No. 2,614,560) and Davis (U.S. Pat. No. 4,867,147).

It is important that mouthguards used for patients be both inexpensive to construct so that they can be disposable; be able to fit all patients, i.e, with different sizes of oral cavities or different numbers and arrangements of remaining teeth using a minimum number of mouthguard models; provide sufficient cushioning to minimize tooth damage; be resilient so as to withstand compression or perforation under biting forces; be flexible so as to allow contouring or bending of the planar single unit to adapt to the intra-oral and extra-oral surfaces; be nontoxic and non irritating to the oral mucosa or skin of the patient; and allow the anesthetized patient to be ventilated or the conscious patient to breathe through his mouth while the mouthguard is positioned in the oral cavity. It is also important that the device prevents the impingement and laceration of oral soft tissues, i.e., tongue, cheeks, and lips.

The mouthguard used should be able to be securely positioned in the oral cavity so as to neither be dislodged posteriorly which could compromise the patient's airway or throat or dislodged anteriorly which could expel the mouthguard from the patient's oral cavity. Additionally, the mouthguard should allow normal oral movements much as speaking, yawning and lateral movements of the mandible. The prior mouthguards generally are deficient in one or more of these aspects.

Minneman's mouthguard (U.S. Pat. No. 5,235,991) has a thin, stiff, generally triangular planar portion capable of deflecting mouth and cheek tissues, with arms along one side of the triangular plane and a single handle at an opposite end of the planar portion from the arms; and a compressible portion located on each arm and extending above and below the planar portion. This mouthguard is designed to prevent tooth and soft tissue injury in patients who are receiving ECT, but does not address the problem of self-inflicted trauma in the conscious patient or mechanical retention of the positioned mouthguard in the oral cavity of the conscious or unconscious patient so that constant supervision and management of the device by a caregiver is not necessary.

It is therefore an object of this invention to provide a mouthguard which can be manufactured inexpensively.

It is a further object of this mouthguard to have a minimum number of intra-oral shapes and sizes in order to be able to fit all patients, i.e., with different sizes of oral cavities or different numbers and arrangements of remaining teeth.

It is a further objective of this invention to provide a mouthguard which is effective in minimizing tooth damage and oral soft tissue damage to tongues, cheeks and lips.

It is a further object of this invention to provide a mouthguard which allows a patient to breathe through his mouth or to be ventilated while the mouthguard is in the patient's oral cavity.

It is a further object of this invention to provide a mouthguard which is resilient and able to withstand compression and perforation under biting forces and be flexible so as to be bendable and adaptable in order to contour to the intra-oral and extra-oral surfaces.

It is a further object of this invention to provide a mouthguard which is non-toxic to intra-oral tissues as well as non-irritating to extra-oral tissues.

It is a further object of this invention to provide a mouthguard which will not obstruct resuscitation or mouth-breathing.

It is a further object of the invention to provide a mouthguard which can be mechanically secured into its position in the oral cavity by a headstrap so as not to be displaced more posteriorly in the oral cavity or expelled out of the mouth.

Other objects and advantages will be more fully apparent from the following disclosure and appended claims.

SUMMARY OF THE INVENTION

The mouth guard of the invention has two main portions: a smaller intra-oral portion and a larger extra-oral portion for placement outside the mouth.

The smaller intra-oral portion is presented in three forms: a first embodiment places the biting forces bilaterally upon the upper and lower anterior teeth, a second embodiment places the biting forces bilaterally upon the upper and lower posterior or molar teeth, and a third embodiment places the biting forces unilaterally upon the upper and lower canine teeth. The intra-oral portion and the extra-oral portion form bilateral narrow indentations at their common connection. These U-shaped spaces receive the corners of the mouth bilaterally.

The invention is flat and relatively thin (approximately 7 mm in thickness) yet the placement of the intra-oral portion between the chewing surfaces of the teeth which correspond to the selected intra-oral embodiment or model prevents the other teeth from coming into contact with one another. The mouthguard is made of a compressible, resilient, flexible material in its preferred embodiment. This flexibility of the material allows the mouthguard to be bent into a 45°–75° angle at the connection between the intra-oral and extra-oral portions to contour the extra-oral portion to the shapes of the lower lip and the cheeks. The central area of the extra-oral portion deflects the lower lip away from the lower anterior teeth.

The extra-oral portion is much larger than the intra-oral portion. This larger surface area aids in the stabilization of the mouthguard and the length of the extra-oral arms makes the movement of the extra-oral aspect intra-orally very difficult.

Oval shaped holes are placed bilaterally in the most distal aspects of the arms of the extra-oral portions. These holes receive a preferably non-elastic head strap which serves to maintain and stabilize the mouthguard in its proper position in the oral cavity.

DETAILED DESCRIPTION OF THE INVENTION AND PREFERRED EMBODIMENTS THEREOF

Mouthguard 20 of the present invention provides a means of placing a cushioning pad between certain upper and lower teeth in the oral cavity thus preventing other opposing teeth in the oral cavity from contracting one another. In particular, the mouthguard's structure provides protection for the teeth and oral soft tissues, i.e., tongue, cheek, and lower lip during forceful closure, biting, clenching and grinding of the jaws in the patient who unconsciously or consciously produces these mouth movements (comatose, decerebrate, generally anesthetized patients or those who have altered sensations of pain and pressure following local dental anesthesia of the mandible). As used herein the words "up" and "down" (and derivative words such as, upper and lower, respectively), and "left", "right", "front", and "back" refer to the mouthguard 20 or one or more parts thereof when oriented for use in the mouth of an upright person.

Figures 1, 3:
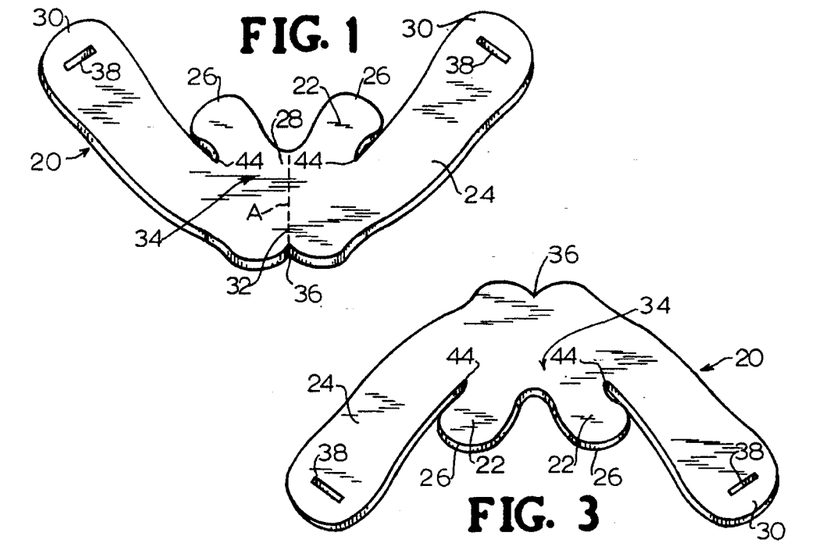
FIG. 1 is a front perspective view of a first embodiment of the mouthguard of the invention which places the mouthguard's intra-oral aspect bilaterally between the upper and lower anterior teeth, i.e. canine to canine.
FIG. 3 is a back perspective view of the first embodiment of the mouthguard of the invention.
Figure 2:
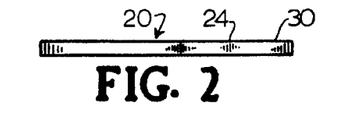
FIG. 2 is an elevational side view of the first embodiment of the mouthguard of the invention.
Figure 4:
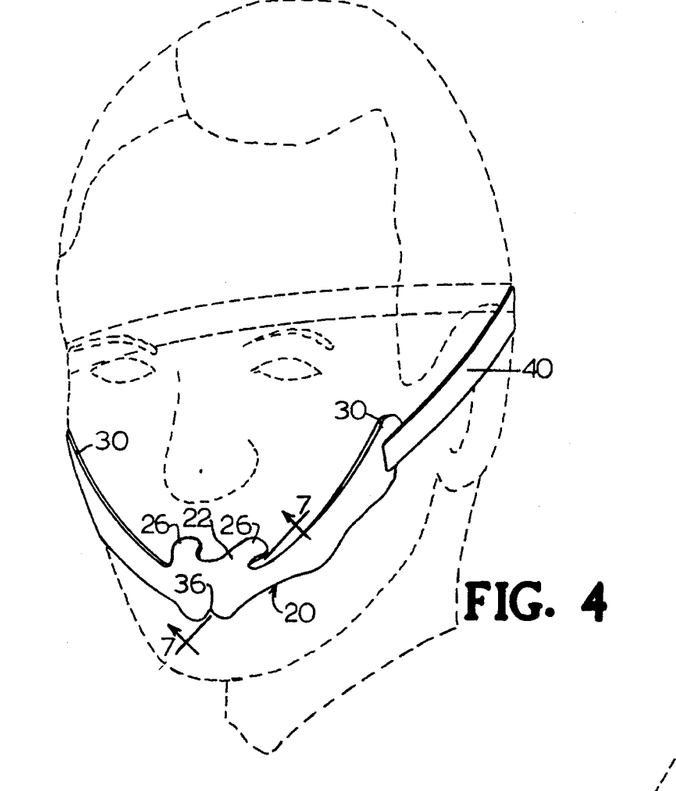
FIG. 4 is a front view of the first embodiment of the mouthguard of the invention showing its location in an oral cavity.
Figure 8:
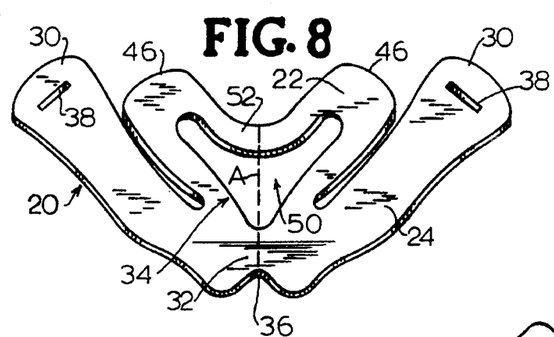
FIG. 8 is a front perspective view of a second embodiment of the mouthguard of the invention which places the mouthguard's intra-oral aspect bilaterally between the upper and lower molar teeth.
Figure 9:
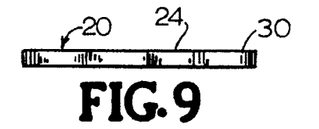
FIG. 9 is an elevational side view of the second embodiment of the mouthguard of the invention.
Figure 10:
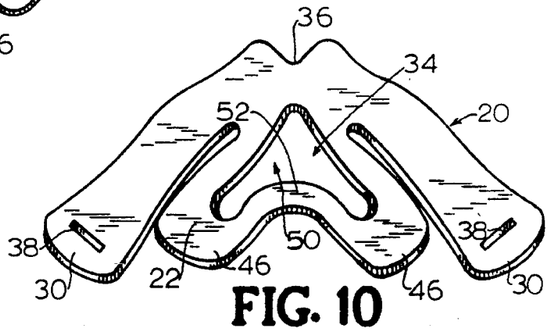
FIG. 10 is a back perspective view of the second embodiment of the mouthguard of the invention.
Figure 11:
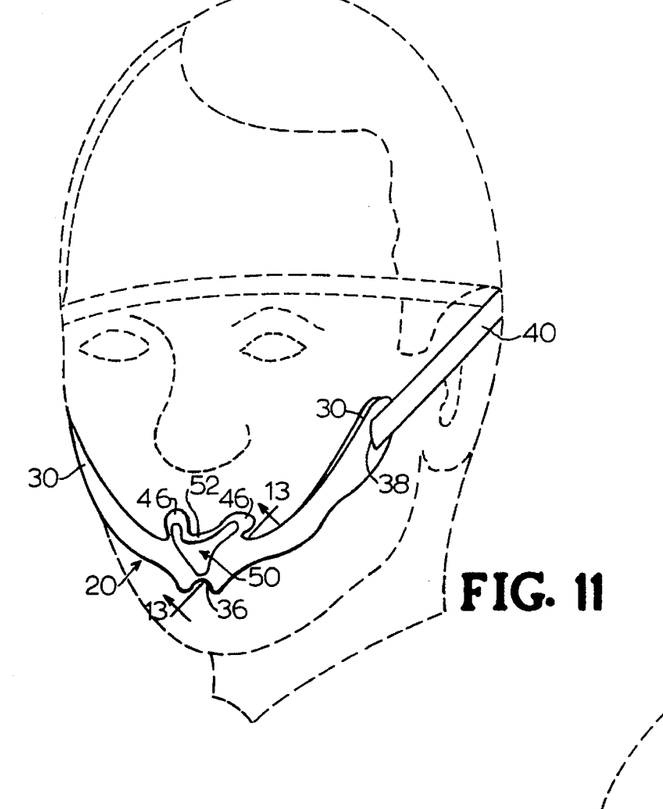
FIG. 11 is a front view of the second embodiment of the mouthguard of the invention showing its location in an oral cavity.

Mouthguard 20 of the invention is preferably planar (FIGS. 2, 9, 15) with an intra-oral portion 22 which is shown in three embodiments having arms 26, 46 and 48 (FIGS. 1, 3–5; FIGS. 8, 10–12; and FIGS. 14, 16–18, respectively). All three embodiments have an extra-oral portion 24. Intra-oral arms 26 and 46 (FIGS. 1, 3–5 and FIGS. 8, 10–12) as well as the extra-oral portion 24 of the first two embodiments are left side/right side mirror images of each other about line A as shown in FIGS. 1 and 8. Therefore, these two models of the mouthguard of the invention may be used with either flat side as the upper side for a particular patient.

As shown in FIGS. 1, 3–5, 8, 10–12, 14, and 16–18, mouthguard 20 of the invention is generally "U" or "V" shaped. The actual shape of the mouthguard, and of each of the two main portions thereof, while being generally U-shaped, broadens out at the "top" of the each "U" (or "V").

There are two opposite indentations 44 (one on the left side and one on the right side of the mouthguard 20) which together form a central constricted area 34 which divides the mouthguard 20 into the two main portions, intra-oral portion 22 and extra-oral portion 24. Constricted area 34 is a very narrow area extending between the intra-oral portion 22 and extra-oral portion 24 of the mouth guard.

Intra-oral portion 22 is generally a broad "U" in shape (FIGS. 1, 3–5, 8, 10–12). Two arms 26 or 46 of the intraoral portion, in the first and second embodiments, respectively, extend an equal distance on either side of line A at the center of the constricted area 28 of the intra-oral portion 22. Arms 26 and 46 are of a sufficient width and length to accommodate most or all of the anterior teeth (canines and incisors) in a person's mouth, so that when the mouthguard is in use the canine and incisor teeth rest upon arms 26 while the other opposing teeth in the oral cavity i.e. premolars and molars, are held apart from one another. The width of arms 26 is sufficient to extend beyond the teeth in order to deflect the lip tissues and depress the tongue away from the teeth. The interior aspect of arms 46 (FIGS. 8, 10–12) is hollow with the exception of the most posterior or distal aspect of each arm which is a solid cushion. The solid cushions at the most posterior aspect of arms 46 accommodate the molars in a person's mouth, so that when the mouthguard is in use the molars rest upon the cushions while the other teeth in the oral cavity, i.e. premolars, canines and incisors, are held apart and rest in hollow space 50. The area surrounding hollow space 50 maintains the integrity of the shape of the intra-oral portion. The back border 52 of this area depresses the tongue, while the front area deflects the cheeks and lips.

Hollow space 50 extends through to central constricted area 34 and into central portion 32 of the mouthguard. The central portion 32 then forms the front border and aids in maintaining the integrity of the shape of the intra-oral portion.

Intra-oral portion 48 of the third embodiment shown in FIGS. 14, and 16–18 is a unilateral arm shaped as a bent-finger-type projection. The tip 54 of the projection extends past the midline A. This unilateral projection is of sufficient width and length to accommodate the upper or lower canine teeth on one side of the oral cavity. The mouthguard may be flipped over to accommodate the upper and lower canine teeth of the opposite side of the mouth. When the mouthguard is in use in a person's mouth, the upper and lower canine teeth on only one side of the mouth rest upon this unilateral arm and the other teeth, i.e., molars, premolars, other canines, and incisors are held apart from one another.

Figure 5:
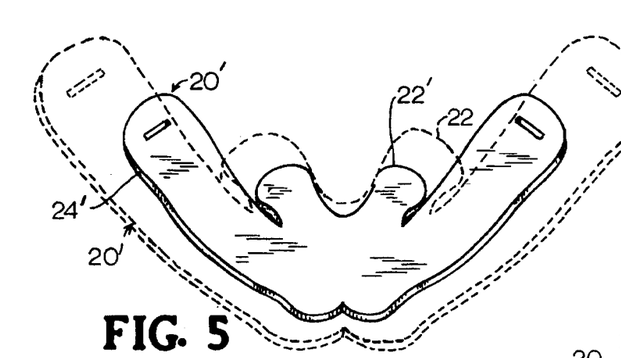
FIG. 5 is a plan view of the first embodiment of the mouthguard of the invention which may be used in a small oral cavity, with a size for a larger oral cavity shown in dotted lines.
Figure 12:
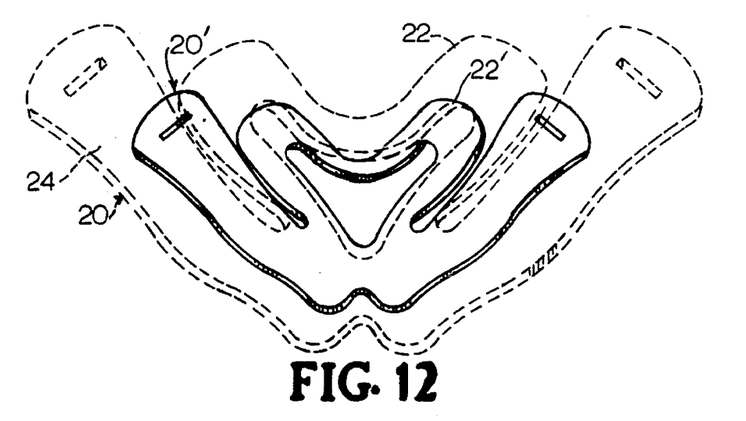
FIG. 12 is a plain view of the second embodiment of the mouthguard of the invention which may be used in a small oral cavity, with a size for a larger oral cavity shown in dotted lines.
Figure 13:
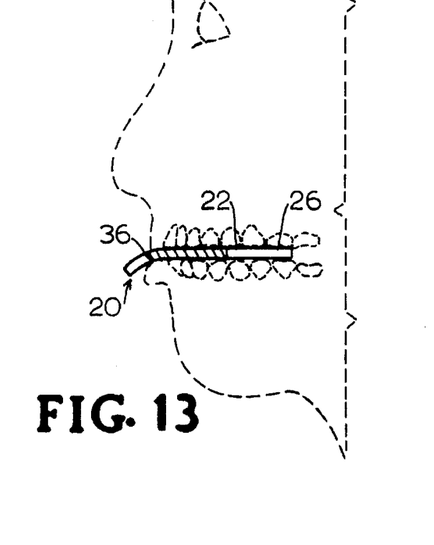
FIG. 13 is a side view of a head of a patient with whom the second embodiment of the mouthguard of the invention is being used.
Figure 18:
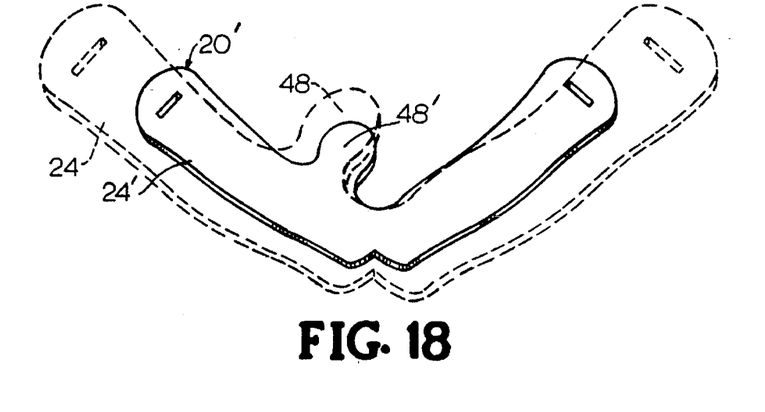
FIG. 18 is a plain view of the mouthguard of the third embodiment of the invention which may be used in a small oral cavity, with a size for a larger oral cavity shown in dotted lines.
Figure 19:
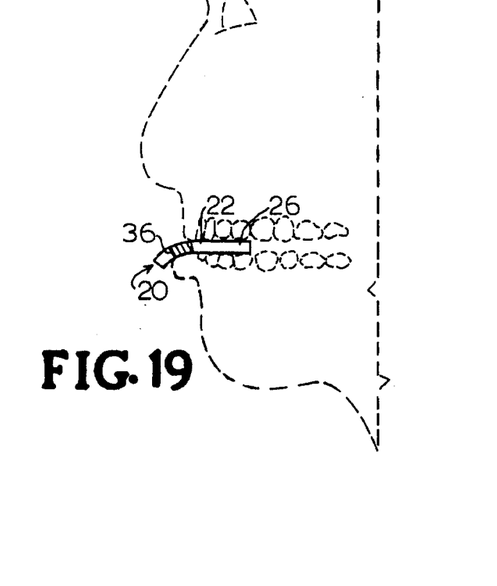
FIG. 19 is a side view of a head of a patient with whom the third embodiment of the mouthguard of the invention is being used.

Extra-oral portion 24 in all embodiments is also generally in the shape of a "U", as is shown most clearly in the solid lines of FIGS. 5, 12 and 18. Arms 30 extending in mirror image on either side of a line A in the center of central portion 32.

The shape of the preferred embodiment of extra-oral portion 24 of the invention varies slightly from a simple "U" shape. Preferably there is a slight indentation 36 in the outer edge of extra-oral portion 24 so that the edge of extraoral portion 22 appears like a shallow "W". The reason for this indentation is to allow flexibility in movement of the device when adapting extra-oral arms 30 to the contour of the chin and cheeks of the user. Indentation 36 also designates the midline of the mouthguard, thus aiding in the proper placement and alignment upon insertion of intra-oral portion 22.

The relative position of each arm 26, 46 or 48 of intraoral portion 22 and the corresponding arm 30 of extra-oral portion 26 deflects the inner surfaces of the cheeks away from the teeth or edentulous ridges to prevent impingement, and intra-oral arms 30 stabilize the position of intra-oral portion in the patient's mouth.

Figure 6:
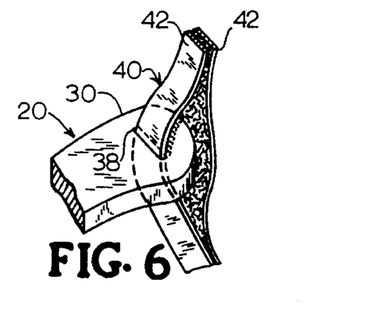
FIG. 6 is a perspective side view of the end of a preferred linear fastening means for the mouthguard of the invention, which places the intra-oral aspect bilaterally between the upper and lower anterior teeth.
Figures 14, 16:
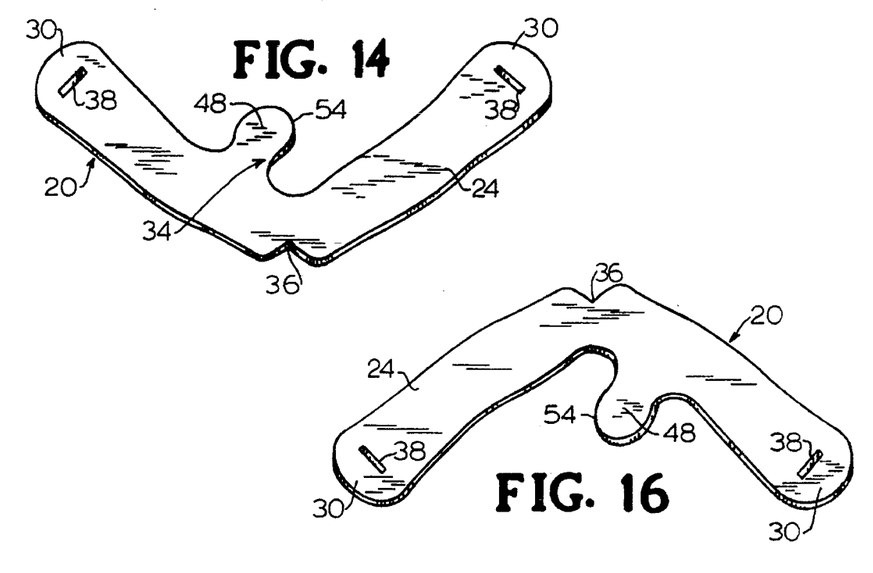
FIG. 14 is a front perspective view of a third embodiment of the mouthguard of the invention which places the mouthguard's intra-oral aspect unilaterally between the upper and lower canine teeth.
FIG. 16 is a back perspective view of the third embodiment of the mouthguard of the invention.
Figure 15:
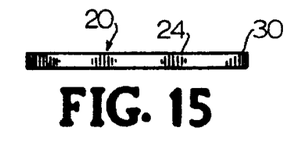
FIG. 15 is an elevational side view of the third embodiment of the mouthguard of the invention.
Figure 17:
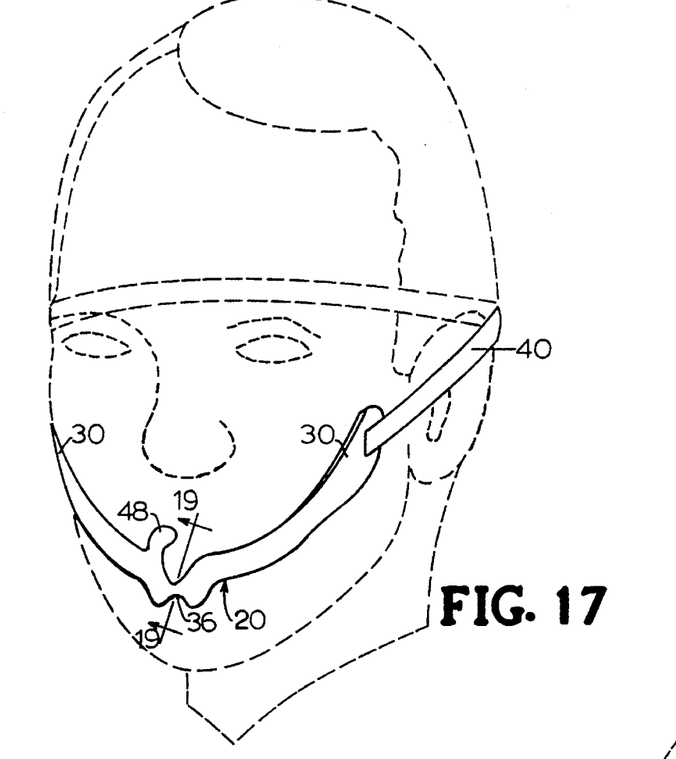
FIG. 17 is a front view of the third embodiment of the mouthguard of the invention showing its location in an oral cavity.

Preferably each extra-oral portion 24 has a hole 38 in each arm extending therethrough as shown in FIGS. 1, 8 and 14, for attachment of a linear fastening means 40 to mouthguard 20. A preferred linear fastening means is made of two matable pieces 42 of interlocking material, such as VEL-CRO™ (FIG. 6). One piece 42 of the interlocking material is preferably threaded through each hole 38 and adjusted to the appropriate position in hole 38 to hold mouthguard 20 in the desired position on the patient. The other piece 42 of interlocking material is then mated with the first piece so that mouthguard 20 is held in the correct position between the mated interlocking pieces 42.

Alternatively, the linear fastening means may be made of a non-elastic fabric with adjustability for example, by means of snaps, buckles, hooks and eyes and the like, threaded through each hole 38 for placement around the back of the head of the patient to hold mouthguard 20 on the patient.

Mouthguard 20 is preferably made in one piece of a material having the compressibility, durability and flexibility of polyethylene foam, rubber or other sturdy but compressible material, and most preferably is made of polyethylene foam. Mouthguard 20 preferably is of uniform thickness throughout, preferably about 5–10 mm thick, and is preferably made in a series of sizes for persons of different mouth sizes. Thus, there are preferably at least two sizes, one for children and one for adults as shown in FIGS. 5, 12 and 18 by the solid and dashed lines, respectively. Mouthguard 20 is also preferably made in several models for persons with different medical conditions and oral behaviors as well as different numbers and arrangements of remaining teeth.

Figure 7:
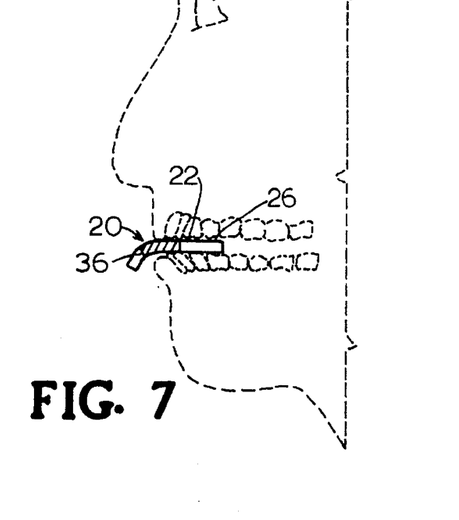
FIG. 7 is a side view of a head of a patient with whom the first embodiment of the mouthguard of the invention is being used.

Thus, with mouthguard 20 held generally horizontally with either flat side of mouthguard 20 uppermost, the invention is used as follows: the medical practitioner holds mouthguard 20 by extra-oral portion 24 and places mouthguard 20 in position in the patient's mouth so that arms 26, 46 or 48 are located inside the mouth along the sides of the mouth, and the flat side of each arm 30 is located outside of the mouth along the cheeks. When the patient's jaws clamp together, the teeth press into each intra-oral portion 22, 46 or 48, respectively, in the three embodiments at the point where they contact mouthguard 20 (see FIGS. 4 and 7). The firmness of the preferred compressible material keeps other teeth from contacting one another thus preventing oral soft tissue from becoming impinged, lacerated, perforated or torn.

Preferred relative dimensions of the invention for a small oral cavity and a larger cavity are shown in FIGS. 5, 12 and 18. Thus small mouth guard 20' has shorter arms 22' (or 46' or 48') and 24' than in the standard adult model shown in dotted lines. In the preferred dimensions, for example, in the first embodiment of the invention the width of each arm 26 at its widest point is about 2–5 cm and the width of each arm 30 at its widest point is about 3 cm. The width of the mouthguard 20 from outermost tip of one arm 30 to the other arm 30 is preferably about 12.5 cm. The width from back to front of the device in the central area is preferably about 5 cm and the width of the arm 44 varies from about 1.5 to 4 cm.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A mouthguard for a patient, comprising a single planar piece of compressible flexible material, said piece comprising an intra-oral portion and an extra-oral portion said intra-oral portion comprising one curved arm and the extra-oral portion comprising two curved arms which extend in mirror image on either side of a line in the center of said extra-oral portion, said extra-oral portion having a W-shaped edge with a central indentation to allow flexibility of the mouthguard, wherein one arm of said extra-oral portion is generally curved around said curved arm of said intra-oral portion, wherein said arm of said intra-oral portion is of a size enabling said arm of said intra-oral portion to fit in the mouth of said patient, and the arm of said intra-oral portion is separated from the extra-oral portion by side indentation, wherein when said mouthguard is placed in the mouth of the patient, the side indentation receives a corner of the mouth and the extra-oral portions extend along the cheeks of the patient on each side of the patient's face.

2. The mouthguard according to claim 1, wherein the extra-oral portion has a hole extending through each arm for attachment of a linear fastening means to the mouthguard.

3. The mouthguard according to claim 2, further comprising a linear fastening means fastened to the mouthguard.

4. The mouthguard according to claim 3, wherein said linear fastening means comprises matable pieces of interlocking material, wherein one of said matable pieces of interlocking material is threaded through each of the holes.

5. The mouthguard according to claim 1, wherein said compressible flexible material is polyethylene foam.

* * * * *